(12) United States Patent
Saroha et al.

(10) Patent No.: US 11,759,174 B2
(45) Date of Patent: Sep. 19, 2023

(54) FLEXIBLE IMAGING ASSEMBLY FOR INTRALUMINAL IMAGING AND ASSOCIATED DEVICES, SYSTEMS, AND METHODS

(71) Applicant: KONINKLIJKE PHILIPS N.V., Eindhoven (NL)

(72) Inventors: Princeton Saroha, Ladera Ranch, CA (US); Jeremy Stigall, Carlsbad, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 400 days.

(21) Appl. No.: 16/336,329

(22) PCT Filed: Sep. 28, 2017

(86) PCT No.: PCT/EP2017/074695
§ 371 (c)(1),
(2) Date: Mar. 25, 2019

(87) PCT Pub. No.: WO2018/060369
PCT Pub. Date: Apr. 5, 2018

(65) Prior Publication Data
US 2019/0231313 A1 Aug. 1, 2019

Related U.S. Application Data

(60) Provisional application No. 62/401,630, filed on Sep. 29, 2016.

(51) Int. Cl.
*A61B 8/00* (2006.01)
*A61B 8/08* (2006.01)
(Continued)

(52) U.S. Cl.
CPC .......... *A61B 8/4494* (2013.01); *A61B 8/0891* (2013.01); *A61B 8/12* (2013.01);
(Continued)

(58) Field of Classification Search
CPC ................ A61B 8/4494; A61B 8/4477; A61B 2562/164; A61B 2562/166; B06B 1/0633; G10K 11/004; H05K 1/189
See application file for complete search history.

(56) References Cited

U.S. PATENT DOCUMENTS

| | | | | |
|---|---|---|---|---|
| 5,857,974 A | * | 1/1999 | Eberle | ................... A61B 1/0011 29/25.35 |
| 6,776,763 B2 | * | 8/2004 | Nix | ....................... B06B 1/0633 29/25.35 |

(Continued)

FOREIGN PATENT DOCUMENTS

| | | |
|---|---|---|
| JP | 2004159837 A | 6/2004 |
| WO | 2007115307 A2 | 10/2007 |

*Primary Examiner* — Serkan Akar
*Assistant Examiner* — Amal Aly Farag

(57) ABSTRACT

An intraluminal imaging device includes a flexible elongate member sized and shaped for insertion into a vessel of a patient, the flexible elongate member including a proximal portion and a distal portion; and an imaging assembly disposed at the distal portion of the flexible elongate member, the imaging assembly including a flex circuit disposed in a rolled configuration, the flex circuit comprising a spine member and a plurality of rib members extending from the spine member. Associated devices, systems, and methods are also provided.

10 Claims, 11 Drawing Sheets

(51) Int. Cl.
  A61B 8/12       (2006.01)
  B06B 1/02       (2006.01)
  B06B 1/06       (2006.01)
  G10K 11/00      (2006.01)
  H05K 1/18       (2006.01)

(52) U.S. Cl.
  CPC ............ *A61B 8/445* (2013.01); *A61B 8/4477* (2013.01); *A61B 8/4488* (2013.01); *A61B 8/54* (2013.01); *B06B 1/0292* (2013.01); *B06B 1/0622* (2013.01); *B06B 1/0633* (2013.01); *G10K 11/004* (2013.01); *B06B 2201/76* (2013.01); *H05K 1/189* (2013.01); *H05K 2201/10151* (2013.01)

(56) References Cited

U.S. PATENT DOCUMENTS

| | | | |
|---|---|---|---|
| 2006/0052707 A1* | 3/2006 | Dickinson | G01S 15/8915 600/466 |
| 2014/0180072 A1* | 6/2014 | Davies | G01S 7/52074 600/424 |
| 2014/0276052 A1* | 9/2014 | Rankin | A61B 18/1492 600/439 |
| 2014/0276085 A1 | 9/2014 | Miller | |
| 2015/0305710 A1 | 10/2015 | Stigall et al. | |
| 2017/0265842 A1* | 9/2017 | Corl | B06B 1/0633 |

* cited by examiner

FLEXIBLE IMAGING ASSEMBLY FOR INTRALUMINAL IMAGING AND ASSOCIATED DEVICES, SYSTEMS, AND METHODS

This application is the U.S. National Phase application under 35 U.S.C. § 371 of International Application No. PCT/EP2017/074695, filed on Sep. 28, 2017, which claims the benefit of Provisional Application Ser. No. 62/401,630, filed Sep. 29, 2016. These applications are hereby incorporated by reference herein.

TECHNICAL FIELD

The present disclosure relates generally to intraluminal imaging and, in particular, to an imaging assembly of an intraluminal imaging device. For example, the imaging assembly can include a flex circuit having spine member and rib members extending from the spine member. The flex circuit structure increases flexibility and maneuverability of the intraluminal imaging device within vessels of a patient.

BACKGROUND

Intravascular ultrasound (IVUS) imaging is widely used in interventional cardiology as a diagnostic tool for assessing a diseased vessel, such as an artery, within the human body to determine the need for treatment, to guide the intervention, and/or to assess its effectiveness. An IVUS device including one or more ultrasound transducers is passed into the vessel and guided to the area to be imaged. The transducers emit ultrasonic energy in order to create an image of the vessel of interest. Ultrasonic waves are partially reflected by discontinuities arising from tissue structures (such as the various layers of the vessel wall), red blood cells, and other features of interest. Echoes from the reflected waves are received by the transducer and passed along to an IVUS imaging system. The imaging system processes the received ultrasound echoes to produce a cross-sectional image of the vessel where the device is placed.

Solid-state (also known as synthetic-aperture) IVUS catheters are one of the two types of IVUS devices commonly used today, the other type being the rotational IVUS catheter. Solid-state IVUS catheters carry a scanner assembly that includes an array of ultrasound transducers distributed around its circumference along with one or more integrated circuit controller chips mounted adjacent to the transducer array. The controllers select individual transducer elements (or groups of elements) for transmitting an ultrasound pulse and for receiving the ultrasound echo signal. By stepping through a sequence of transmit-receive pairs, the solid-state IVUS system can synthesize the effect of a mechanically scanned ultrasound transducer but without moving parts (hence the solid-state designation). Since there is no rotating mechanical element, the transducer array can be placed in direct contact with the blood and vessel tissue with minimal risk of vessel trauma. Furthermore, because there is no rotating element, the electrical interface is simplified. The solid-state scanner can be wired directly to the imaging system with a simple electrical cable and a standard detachable electrical connector, rather than the complex rotating electrical interface required for a rotational IVUS device.

Manufacturing an intraluminal imaging device that can efficiently traverse physiology within the human body is challenging. In that regard, components at the distal portion of the imaging device causes an area of high rigidity in the intraluminal device, which increase the likelihood of kinking as the intraluminal device is steered through vasculature. Also, in most phased array IVUS devices, there is a compromise between usability, image quality/resolution, and stiff length. Adding more transducer elements usually improves image quality but also increases stiff length, which makes the intraluminal device less maneuverable in smaller and more tortuous anatomical pathways.

SUMMARY

The invention provides imaging devices, systems, and related methods that overcome the limitations associated with a rigid imaging assembly while also achieving high image quality and maneuverability.

Embodiments of the present disclosure provide an improved intraluminal ultrasound imaging system for generating images of a blood vessel. A distal portion of an intraluminal imaging device includes an imaging assembly having a flex circuit. The flex circuit is a flexible substrate on which ultrasound transducers and electronic controllers for the transducers are positioned. The flex circuit includes a spine member and multiple rib members extending from the spine member. The transducers and the controllers are positioned on the rib members. The spine member includes conductive traces allowing electrical communication between the transducers and the controllers. The spine/rib structure of the imaging assembly allows for increased flexibility and maneuverability within vasculature, while preserving/improving image quality.

In one embodiment, an intraluminal imaging device is provided. The intraluminal imaging device includes a flexible elongate member configured for insertion into a vessel of a patient, the flexible elongate member including a proximal portion and a distal portion; and an imaging assembly comprising a flex circuit disposed in a rolled configuration at the distal portion of the flexible elongate member, the flex circuit comprising a spine member and a plurality of rib members extending from the spine member.

In some embodiments, at least one of the plurality of rib members comprises a plurality of ultrasound transducers, at least one of the plurality of rib members comprises a plurality of controllers, and the spine member comprises a plurality of conductive traces facilitating communication between the plurality of the ultrasound transducers and the plurality of controllers. In some embodiments, a proximal-most rib member and a distal-most rib member of the plurality of rib members comprises a plurality of ultrasound transducers. In some embodiments, a central rib member of the plurality of rib members comprises a plurality of ultrasound transducers. In some embodiments, the plurality of rib members comprises five rib members. In some embodiments, different ones of the plurality of rib members of the flex circuit comprise different types of ultrasound transducers. In some embodiments, the spine member of the flex circuit extends a length of a longitudinal axis of the imaging assembly. In some embodiments, the plurality of rib members extends from the spine member in a direction transverse to the longitudinal axis of the imaging assembly. In some embodiments, the plurality of rib members at least partially circumscribe or extend around the longitudinal axis of the imaging assembly. In some embodiments, the plurality of rib members are longitudinally spaced from one another.

In one embodiment, a system is provided. The system includes an intraluminal imaging device, including: a flexible elongate member; an imaging assembly disposed at a distal portion of the flexible elongate member and defining a longitudinal axis, the imaging assembly including a flex circuit that comprises a spine member extending a length of the longitudinal axis and a plurality of rib members at least partially circumscribing or extending around the longitudinal axis; and a computer in communication with the imaging assembly to control the imaging assembly to obtain an intraluminal image.

In some embodiments, a first rib member of the plurality of rib members comprises a first plurality of ultrasound transducers, a second rib member of the plurality of rib members comprises a second plurality of ultrasound transducers, at least one of the plurality of rib members comprises a plurality of controllers, and the spine member comprises a plurality of conductive traces facilitating communication between the first and second pluralities of the ultrasound transducers and the plurality of controllers. In some embodiments, the computer is operable to control the first and second pluralities of ultrasound transducers to simultaneously emit ultrasound energy and to receive ultrasound echoes associated with the emitted ultrasound energy. In some embodiments, the computer is operable to control the first and second pluralities of ultrasound transducers to independently emit ultrasound energy and to receive ultrasound echoes associated with the emitted ultrasound energy. In some embodiments, the computer is operable to independently control a selected ultrasound transducer of each of the first and second pluralities of ultrasound transducers to emit ultrasound energy and to receive ultrasound echoes associated with the emitted ultrasound energy. In some embodiments, the selected ultrasound transducers of the first and second pluralities of ultrasound transducers are aligned.

In one embodiment, a method of intraluminal imaging is provided. The method includes controlling a first plurality of ultrasound transducers of an imaging assembly of an intraluminal device to emit ultrasound energy within a vessel of a patient, wherein imaging assembly comprises a flex circuit including a spine member and plurality of rib members, wherein the first plurality of ultrasound transducers are disposed on at least one of the plurality of rib members; and receiving ultrasound echoes associated with the emitted ultrasound energy; and generating an intraluminal image based on the received ultrasound echoes.

In some embodiments, the first plurality of ultrasound transducers are disposed on a first rib member of the plurality of rib members, and wherein a second plurality of ultrasound transducers are disposed on a second rib member of the plurality of rib members, the method further comprising: controlling, independently of the first plurality of ultrasound transducers, the second plurality of ultrasound transducers of the imaging assembly to emit ultrasound energy within the vessel. In some embodiments, the first plurality of ultrasound transducers are disposed on a first rib member of the plurality of rib members, and wherein a second plurality of ultrasound transducers are disposed on a second rib member of the plurality of rib members, the method further comprising: controlling, simultaneously as the first plurality of ultrasound transducers, the second plurality of ultrasound transducers of the imaging assembly to emit ultrasound energy within the vessel. In some embodiments, the first plurality of ultrasound transducers are disposed on first and second rib members of the plurality of rib members, and wherein the first plurality of ultrasound transducers are aligned.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
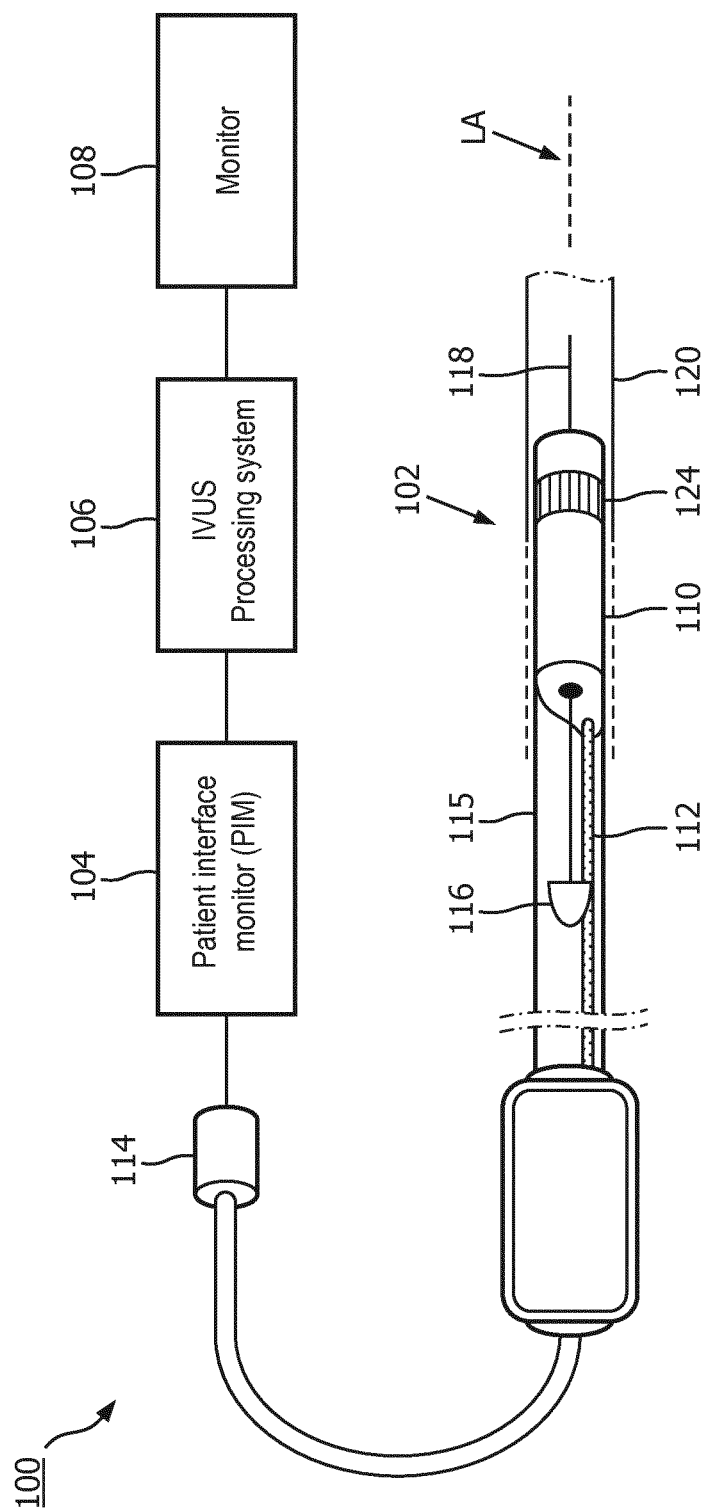
FIG. 1 is a diagrammatic schematic view of an imaging system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

The present disclosure describes an imaging assembly for an intraluminal imaging device. The imaging assembly includes a flex circuit positioned at a distal portion of a flexible elongate member. When intraluminal device is assembled, the flex circuit is arranged in a rolled configuration around a longitudinal axis of the flexible elongate member. The flex circuit includes a spine member and multiple rib members extending from the spine member. The spine member is extends longitudinally along the intraluminal device. The rib members at least partially circumscribe or extend around the intraluminal device when the flex circuit is arranged in the rolled configuration. The flex circuit can be characterized as having a wishbone-like structure. The rib members can be spaced from one another. The space between the rib members can vary as the imaging assembly traverses tortuous vasculature. Each of the rib members can include ultrasound transducer elements and/or electronic controllers that control the transducer elements. The flex circuit, including the spine member, includes conductive traces that facilitate electrical communication between the transducers and the controllers.

The intraluminal imaging device described herein achieves numerous advantages. For example, the spine/rib structure of the flex circuit allows for cross-sectional imaging within the vessel. Additionally, by positioning the transducer elements on multiple rib members, the axial and/or lateral imaging area, quality, and/or resolution can be improved relative to conventional phased array IVUS devices. The structure allows additional transducer elements to be added to the flex circuit without sacrificing flexibility for the imaging assembly. In that regard, the flexibility is increased relative to conventional phase array IVUS devices by spacing the rib members apart. That is, the distance between the rib members can vary to allow the imaging assembly to flexes/bends within vessels of the patient body. The increased flexibility allows a physician to maneuver the intraluminal device more easily within the patient body.

FIG. 1 is a diagrammatic schematic view of an intravascular ultrasound (IVUS) imaging system 100, according to aspects of the present disclosure. The IVUS imaging system 100 may include a solid-state IVUS device 102 such as a catheter, guide wire, or guide catheter, a patient interface module (PIM) 104, an IVUS processing system or console 106, and a monitor 108.

At a high level, the IVUS device 102 emits ultrasonic energy from a transducer array 124 included in scanner assembly 110 mounted near a distal end of the catheter device. The ultrasonic energy is reflected by tissue structures in the medium, such as a vessel 120, surrounding the scanner assembly 110, and the ultrasound echo signals are received by the transducer array 124. The PIM 104 transfers the received echo signals to the console or computer 106 where the ultrasound image (including the flow information) is reconstructed and displayed on the monitor 108. The console or computer 106 can include a processor and a memory. The computer or computing device 106 can be operable to facilitate the features of the IVUS imaging system 100 described herein. For example, the processor can execute computer readable instructions stored on the non-transitory tangible computer readable medium.

The PIM 104 facilitates communication of signals between the IVUS console 106 and the scanner assembly 110 included in the IVUS device 102. This communication includes the steps of: (1) providing commands to integrated circuit controller chip(s) 206A, 206B, illustrated in FIG. 2, included in the scanner assembly 110 to select the particular transducer array element(s) to be used for transmit and receive, (2) providing the transmit trigger signals to the integrated circuit controller chip(s) 206A, 206B included in the scanner assembly 110 to activate the transmitter circuitry to generate an electrical pulse to excite the selected transducer array element(s), and/or (3) accepting amplified echo signals received from the selected transducer array element(s) via amplifiers included on the integrated circuit controller chip(s) 126 of the scanner assembly 110. In some embodiments, the PIM 104 performs preliminary processing of the echo data prior to relaying the data to the console 106. In examples of such embodiments, the PIM 104 performs amplification, filtering, and/or aggregating of the data. In an embodiment, the PIM 104 also supplies high- and low-voltage DC power to support operation of the device 102 including circuitry within the scanner assembly 110.

The IVUS console 106 receives the echo data from the scanner assembly 110 by way of the PIM 104 and processes the data to reconstruct an image of the tissue structures in the medium surrounding the scanner assembly 110. The console 106 outputs image data such that an image of the vessel 120, such as a cross-sectional image of the vessel 120, is displayed on the monitor 108. Vessel 120 may represent fluid filled or surrounded structures, both natural and man-made. The vessel 120 may be within a body of a patient. The vessel 120 may be a blood vessel, as an artery or a vein of a patient's vascular system, including cardiac vasculature, peripheral vasculature, neural vasculature, renal vasculature, and/or or any other suitable lumen inside the body. For example, the device 102 may be used to examine any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood, chambers or other parts of the heart, and/or other systems of the body. In addition to natural structures, the device 102 may be may be used to examine man-made structures such as, but without limitation, heart valves, stents, shunts, filters and other devices.

Figure 2:
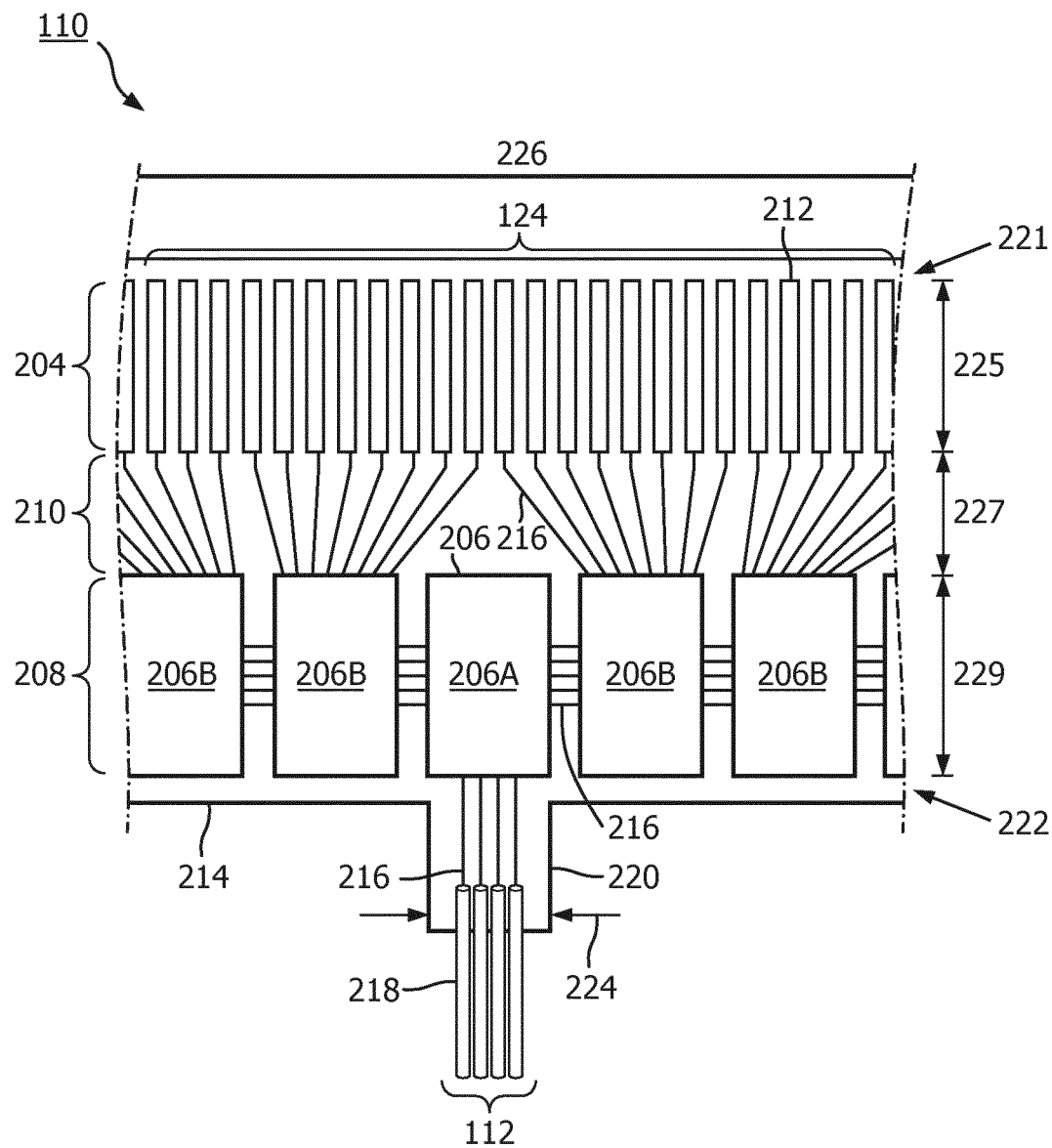
FIG. 2 is a diagrammatic top view of a scanner assembly in a flat configuration, according to aspects of the present disclosure.

In some embodiments, the IVUS device includes some features similar to traditional solid-state IVUS catheters, such as the EagleEye® catheter available from Volcano Corporation and those disclosed in U.S. Pat. No. 7,846,101 hereby incorporated by reference in its entirety. For example, the IVUS device 102 includes the scanner assembly 110 near a distal end of the device 102 and a transmission line bundle 112 extending along the longitudinal body of the device 102. The transmission line bundle or cable 112 can include a plurality of conductors, including one, two, three, four, five, six, seven, or more conductors 218 (FIG. 2). It is understood that any suitable gauge wire can be used for the conductors 218. In an embodiment, the cable 112 can include a four-conductor transmission line arrangement with, e.g., 41 AWG gauge wires. In an embodiment, the cable 112 can include a seven-conductor transmission line arrangement utilizing, e.g., 44 AWG gauge wires. In some embodiments, 43 AWG gauge wires can be used.

The transmission line bundle 112 terminates in a PIM connector 114 at a proximal end of the device 102. The PIM connector 114 electrically couples the transmission line bundle 112 to the PIM 104 and physically couples the IVUS device 102 to the PIM 104. In an embodiment, the IVUS device 102 further includes a guide wire exit port 116. Accordingly, in some instances the IVUS device is a rapid-exchange catheter. The guide wire exit port 116 allows a guide wire 118 to be inserted towards the distal end in order to direct the device 102 through the vessel 120.

The IVUS device 102 includes a flexible elongate member 115 having a proximal portion and a distal portion. The scanner assembly or imaging assembly 110 is positioned at a distal portion of the flexible elongate member 115. The flexible elongate member 115 includes a longitudinal axis LA. The longitudinal axis LA may be associated with the IVUS device 102 and/or the scanner assembly or imaging assembly 110.

Figure 3:
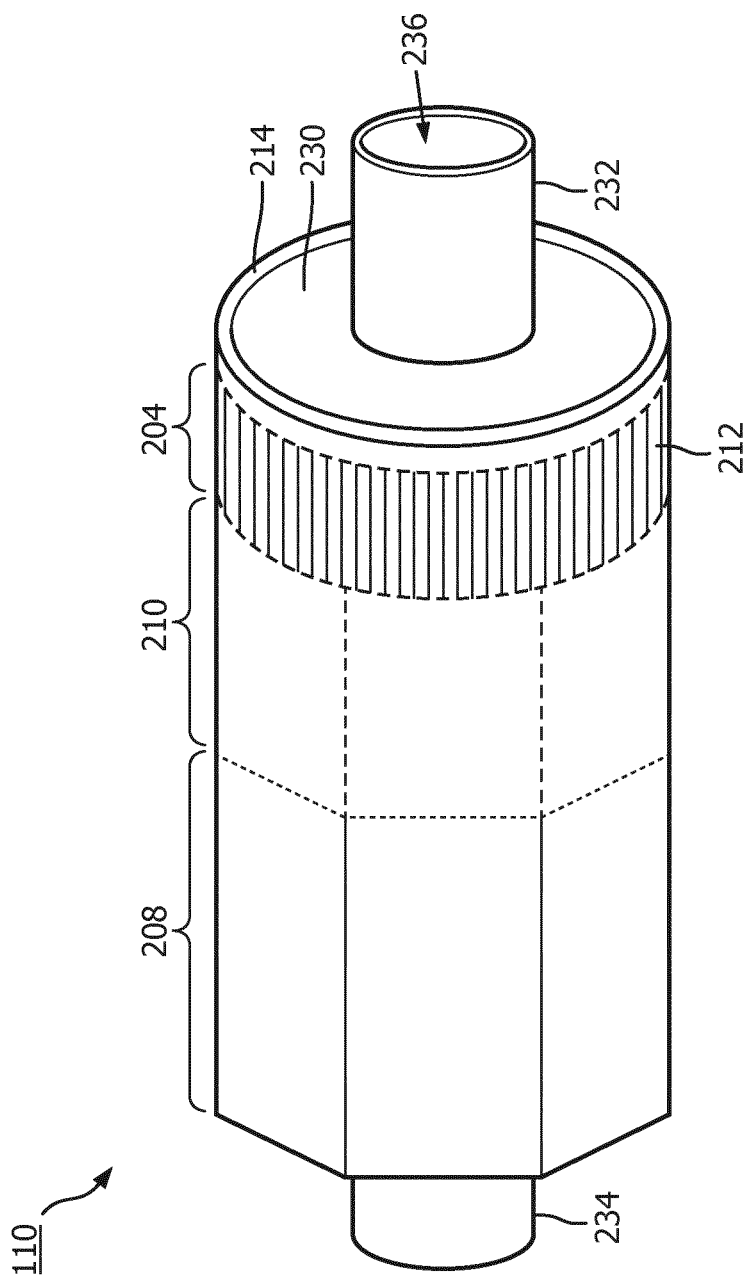
FIG. 3 is a diagrammatic side view of a scanner assembly in a rolled configuration around a support member, according to aspects of the present disclosure.

FIG. 2 is a top view of a portion of an ultrasound scanner assembly 110 according to an embodiment of the present disclosure. The assembly 110 includes a transducer array 124 formed in a transducer region 204 and transducer control logic dies 206 (including dies 206A and 206B) formed in a control region 208, with a transition region 210 disposed therebetween. The transducer control logic dies 206 and the transducers 212 are mounted on a flex circuit 214 that is shown in a flat configuration in FIG. 2. FIG. 3 illustrates a rolled configuration of the flex circuit 214. The transducer array 202 is a non-limiting example of a medical sensor element and/or a medical sensor element array. The transducer control logic dies 206 is a non-limiting example of a control circuit. The transducer region 204 is disposed adjacent a distal portion 221 of the flex circuit 214. The control region 208 is disposed adjacent the proximal portion 222 of the flex circuit 214. The transition region 210 is disposed between the control region 208 and the transducer region 204. Dimensions of the transducer region 204, the control region 208, and the transition region 210 (e.g., lengths 225, 227, 229) can vary in different embodiments. In some embodiments, the lengths 225, 227, 229 can be substantially similar or a length 227 of the transition region 210 can be greater than lengths 225, 229 of the transducer region and controller region, respectively. While the imaging assembly 110 is described as including a flex circuit, it is understood that the transducers and/or controllers may be arranged to form the imaging assembly 110 in other configurations, including those omitting a flex circuit.

The transducer array 124 may include any number and type of ultrasound transducers 212, although for clarity only a limited number of ultrasound transducers are illustrated in FIG. 2. In an embodiment, the transducer array 124 includes 64 individual ultrasound transducers 212. In a further embodiment, the transducer array 124 includes 32 ultrasound transducers 212. Other numbers are both contemplated and provided for. With respect to the types of transducers, in an embodiment, the ultrasound transducers 212 are piezoelectric micromachined ultrasound transducers (PMUTs) fabricated on a micro electromechanical system (MEMS) substrate using a polymer piezoelectric material, for example as disclosed in U.S. Pat. No. 6,641,540, which is hereby incorporated by reference in its entirety. In alternate embodiments, the transducer array includes piezoelectric zirconate transducers (PZT) transducers such as bulk PZT transducers, capacitive micromachined ultrasound transducers (cMUTs), single crystal piezoelectric materials, other suitable ultrasound transmitters and receivers, and/or combinations thereof.

The scanner assembly 110 may include various transducer control logic, which in the illustrated embodiment is divided into discrete control logic dies 206. In various examples, the control logic of the scanner assembly 110 performs: decoding control signals sent by the PIM 104 across the cable 112, driving one or more transducers 212 to emit an ultrasonic signal, selecting one or more transducers 212 to receive a reflected echo of the ultrasonic signal, amplifying a signal representing the received echo, and/or transmitting the signal to the PIM across the cable 112. In the illustrated embodiment, a scanner assembly 110 having 64 ultrasound transducers 212 divides the control logic across nine control logic dies 206, of which five are shown in FIG. 2. Designs incorporating other numbers of control logic dies 206 including 8, 9, 16, 17 and more are utilized in other embodiments. In general, the control logic dies 206 are characterized by the number of transducers they are capable of driving, and exemplary control logic dies 206 drive 4, 8, and/or 16 transducers.

The control logic dies are not necessarily homogenous. In some embodiments, a single controller is designated a master control logic die 206A and contains the communication interface for the cable 112. Accordingly, the master control circuit may include control logic that decodes control signals received over the cable 112, transmits control responses over the cable 112, amplifies echo signals, and/or transmits the echo signals over the cable 112. The remaining controllers are slave controllers 206B. The slave controllers 206B may include control logic that drives a transducer 212 to emit an ultrasonic signal and selects a transducer 212 to receive an echo. In the depicted embodiment, the master controller 206A does not directly control any transducers 212. In other embodiments, the master controller 206A drives the same number of transducers 212 as the slave controllers 206B or drives a reduced set of transducers 212 as compared to the slave controllers 206B. In an exemplary embodiment, a single master controller 206A and eight slave controllers 206B are provided with eight transducers assigned to each slave controller 206B.

The flex circuit 214, on which the transducer control logic dies 206 and the transducers 212 are mounted, provides structural support and interconnects for electrical coupling. The flex circuit 214 may be constructed to include a film layer of a flexible polyimide material such as KAPTON™ (trademark of DuPont). Other suitable materials include polyester films, polyimide films, polyethylene napthalate films, or polyetherimide films, other flexible printed semiconductor substrates as well as products such as Upilex® (registered trademark of Ube Industries) and TEFLON® (registered trademark of E.I. du Pont). In the flat configuration illustrated in FIG. 2, the flex circuit 214 has a generally rectangular shape. As shown and described herein, the flex circuit 214 is configured to be wrapped around a support member 230 (FIG. 3) to form a cylindrical toroid in some instances. Therefore, the thickness of the film layer of the flex circuit 214 is generally related to the degree of curvature in the final assembled scanner assembly 110. In some embodiments, the film layer is between 5 μm and 100 μm, with some particular embodiments being between 12.7 μm and 25.1 μm.

To electrically interconnect the control logic dies 206 and the transducers 212, in an embodiment, the flex circuit 214 further includes conductive traces 216 formed on the film layer that carry signals between the control logic dies 206 and the transducers 212. In particular, the conductive traces 216 providing communication between the control logic dies 206 and the transducers 212 extend along the flex circuit 214 within the transition region 210. In some instances, the conductive traces 216 can also facilitate electrical communication between the master controller 206A and the slave controllers 206B. The conductive traces 216 can also provide a set of conductive pads that contact the conductors 218 of cable 112 when the conductors 218 of the cable 112 are mechanically and electrically coupled to the flex circuit 214. Suitable materials for the conductive traces 216 include copper, gold, aluminum, silver, tantalum, nickel, and tin, and may be deposited on the flex circuit 214 by processes such as sputtering, plating, and etching. In an embodiment, the flex circuit 214 includes a chromium adhesion layer. The width and thickness of the conductive traces 216 are selected to provide proper conductivity and resilience when the flex circuit 214 is rolled. In that regard, an exemplary range for the thickness of a conductive trace 216 and/or conductive pad is between 10-50 µm. For example, in an embodiment, 20 µm conductive traces 216 are separated by 20 µm of space. The width of a conductive trace 216 on the flex circuit 214 may be further determined by the width of the conductor 218 to be coupled to the trace/pad.

The flex circuit 214 can include a conductor interface 220 in some embodiments. The conductor interface 220 can be a location of the flex circuit 214 where the conductors 218 of the cable 112 are coupled to the flex circuit 214. For example, the bare conductors of the cable 112 are electrically coupled to the flex circuit 214 at the conductor interface 220. The conductor interface 220 can be tab extending from the main body of flex circuit 214. In that regard, the main body of the flex circuit 214 can refer collectively to the transducer region 204, controller region 208, and the transition region 210. In the illustrated embodiment, the conductor interface 220 extends from the proximal portion 222 of the flex circuit 214. In other embodiments, the conductor interface 220 is positioned at other parts of the flex circuit 214, such as the distal portion 221, or the flex circuit 214 omits the conductor interface 220. A value of a dimension of the tab or conductor interface 220, such as a width 224, can be less than the value of a dimension of the main body of the flex circuit 214, such as a width 226. In some embodiments, the substrate forming the conductor interface 220 is made of the same material(s) and/or is similarly flexible as the flex circuit 214. In other embodiments, the conductor interface 220 is made of different materials and/or is comparatively more rigid than the flex circuit 214. For example, the conductor interface 220 can be made of a plastic, thermoplastic, polymer, hard polymer, etc., including polyoxymethylene (e.g., DELRIN®), polyether ether ketone (PEEK), nylon, and/or other suitable materials. As described in greater detail herein, the support member 230, the flex circuit 214, the conductor interface 220 and/or the conductor(s) 218 can be variously configured to facilitate efficient manufacturing and operation of the scanner assembly 110.

Figure 4:
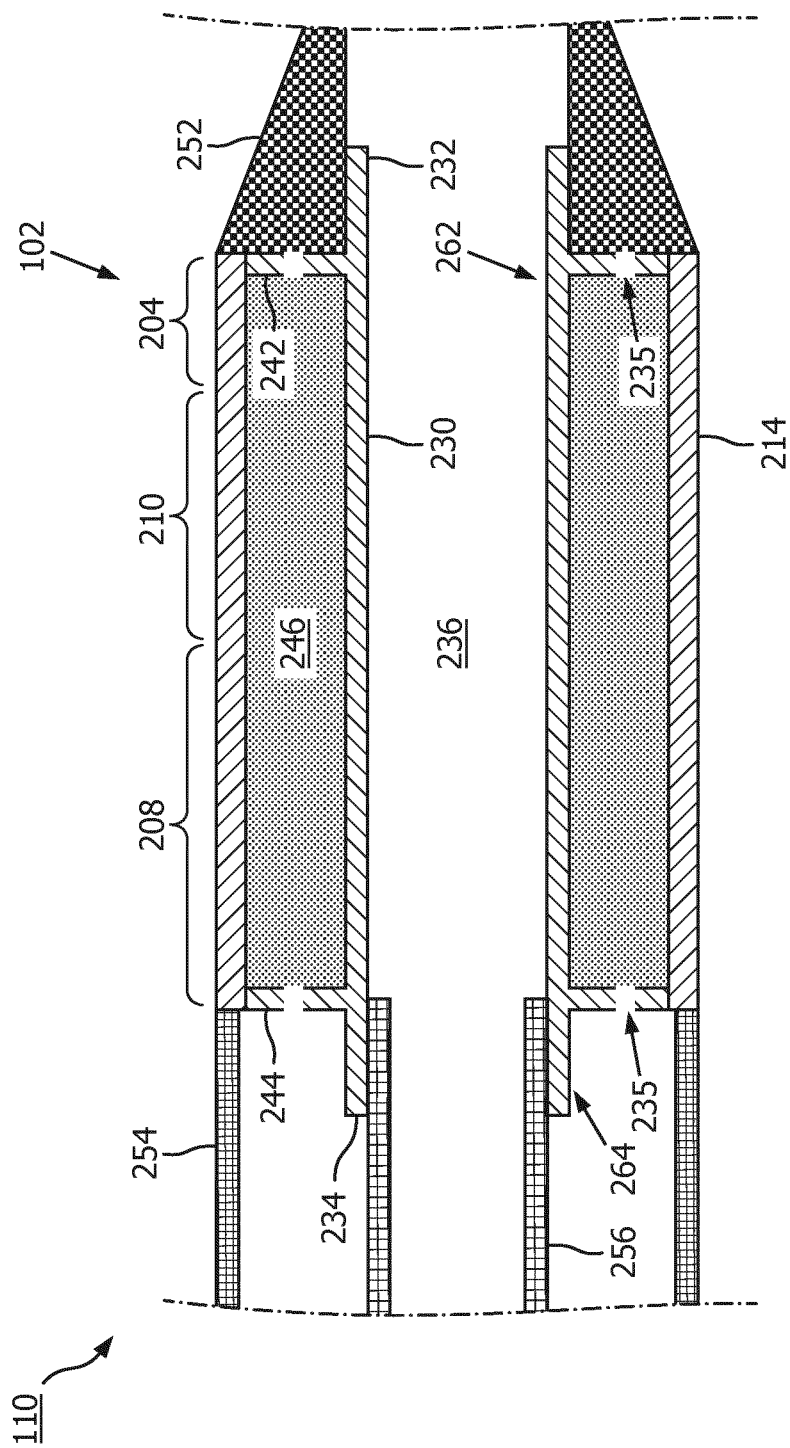
FIG. 4 is a diagrammatic cross-sectional side view of a distal portion of an intraluminal device, according to aspects of the present disclosure.

In some instances, the scanner assembly 110 is transitioned from a flat configuration (FIG. 2) to a rolled or more cylindrical configuration (FIGS. 3 and 4). For example, in some embodiments, techniques are utilized as disclosed in one or more of U.S. Pat. No. 6,776,763, titled "ULTRASONIC TRANSDUCER ARRAY AND METHOD OF MANUFACTURING THE SAME" and U.S. Pat. No. 7,226,417, titled "HIGH RESOLUTION INTRAVASCULAR ULTRASOUND TRANSDUCER ASSEMBLY HAVING A FLEXIBLE SUBSTRATE," each of which is hereby incorporated by reference in its entirety.

As shown in FIGS. 3 and 4, the flex circuit 214 is positioned around the support member 230 in the rolled configuration. FIG. 3 is a diagrammatic side view with the flex circuit 214 in the rolled configuration around the support member 230, according to aspects of the present disclosure. FIG. 4 is a diagrammatic cross-sectional side view of a distal portion of the IVUS device 102, including the flex circuit 214 and the support member 230, according to aspects of the present disclosure.

The support member 230 can be referenced as a unibody in some instances. The support member 230 can be composed of a metallic material, such as stainless steel, or non-metallic material, such as a plastic or polymer as described in U.S. Provisional Application No. 61/985,220, "Pre-Doped Solid Substrate for Intravascular Devices," filed Apr. 28, 2014, the entirety of which is hereby incorporated by reference herein. The support member 230 can be ferrule having a distal portion 262 and a proximal portion 264. The support member 230 can define a lumen 236 extending longitudinally therethrough. The lumen 236 is in communication with the exit port 116 and is sized and shaped to receive the guide wire 118 (FIG. 1). The support member 230 can be manufactured accordingly to any suitable process. For example, the support member 230 can be machined, such as by removing material from a blank to shape the support member 230, or molded, such as by an injection molding process. In some embodiments, the support member 230 may be integrally formed as a unitary structure, while in other embodiments the support member 230 may be formed of different components, such as a ferrule and stands 242, 244, that are fixedly coupled to one another.

Stands 242, 244 that extend vertically are provided at the distal and proximal portions 262, 264, respectively, of the support member 230. The stands 242, 244 elevate and support the distal and proximal portions of the flex circuit 214. In that regard, portions of the flex circuit 214, such as the transducer portion 204, can be spaced from a central body portion of the support member 230 extending between the stands 242, 244. The stands 242, 244 can have the same outer diameter or different outer diameters. For example, the distal stand 242 can have a larger or smaller outer diameter than the proximal stand 244. To improve acoustic performance, any cavities between the flex circuit 214 and the surface of the support member 230 are filled with a backing material 246. The liquid backing material 246 can be introduced between the flex circuit 214 and the support member 230 via passageways 235 in the stands 242, 244. In some embodiments, suction can be applied via the passageways 235 of one of the stands 242, 244, while the liquid backing material 246 is fed between the flex circuit 214 and the support member 230 via the passageways 235 of the other of the stands 242, 244. The backing material can be cured to allow it to solidify and set. In various embodiments, the support member 230 includes more than two stands 242, 244, only one of the stands 242, 244, or neither of the stands. In that regard the support member 230 can have an increased diameter distal portion 262 and/or increased diameter proximal portion 264 that is sized and shaped to elevate and support the distal and/or proximal portions of the flex circuit 214.

The support member 230 can be substantially cylindrical in some embodiments. Other shapes of the support member 230 are also contemplated including geometrical, non-geometrical, symmetrical, non-symmetrical, cross-sectional profiles. Different portions the support member 230 can be variously shaped in other embodiments. For example, the proximal portion 264 can have a larger outer diameter than the outer diameters of the distal portion 262 or a central portion extending between the distal and proximal portions 262, 264. In some embodiments, an inner diameter of the support member 230 (e.g., the diameter of the lumen 236) can correspondingly increase or decrease as the outer diameter changes. In other embodiments, the inner diameter of the support member 230 remains the same despite variations in the outer diameter.

A proximal inner member 256 and a proximal outer member 254 are coupled to the proximal portion 264 of the support member 230. The proximal inner member 256 and/or the proximal outer member 254 can be flexible elongate member that extend from proximal portion of the IVUS device 102, such as the proximal connector 114, to the imaging assembly 110. For example, the proximal inner member 256 can be received within a proximal flange 234. The proximal outer member 254 abuts and is in contact with the flex circuit 214. A distal member 252 is coupled to the distal portion 262 of the support member 230. The distal member 252 can be a flexible component that defines a distal most portion of the IVUS device 102. For example, the distal member 252 is positioned around the distal flange 232. The distal member 252 can abut and be in contact with the flex circuit 214 and the stand 242. The distal member 252 can be the distal-most component of the IVUS device 102.

One or more adhesives can be disposed between various components at the distal portion of the IVUS device 102. For example, one or more of the flex circuit 214, the support member 230, the distal member 252, the proximal inner member 256, and/or the proximal outer member 254 can be coupled to one another via an adhesive.

Figure 5:
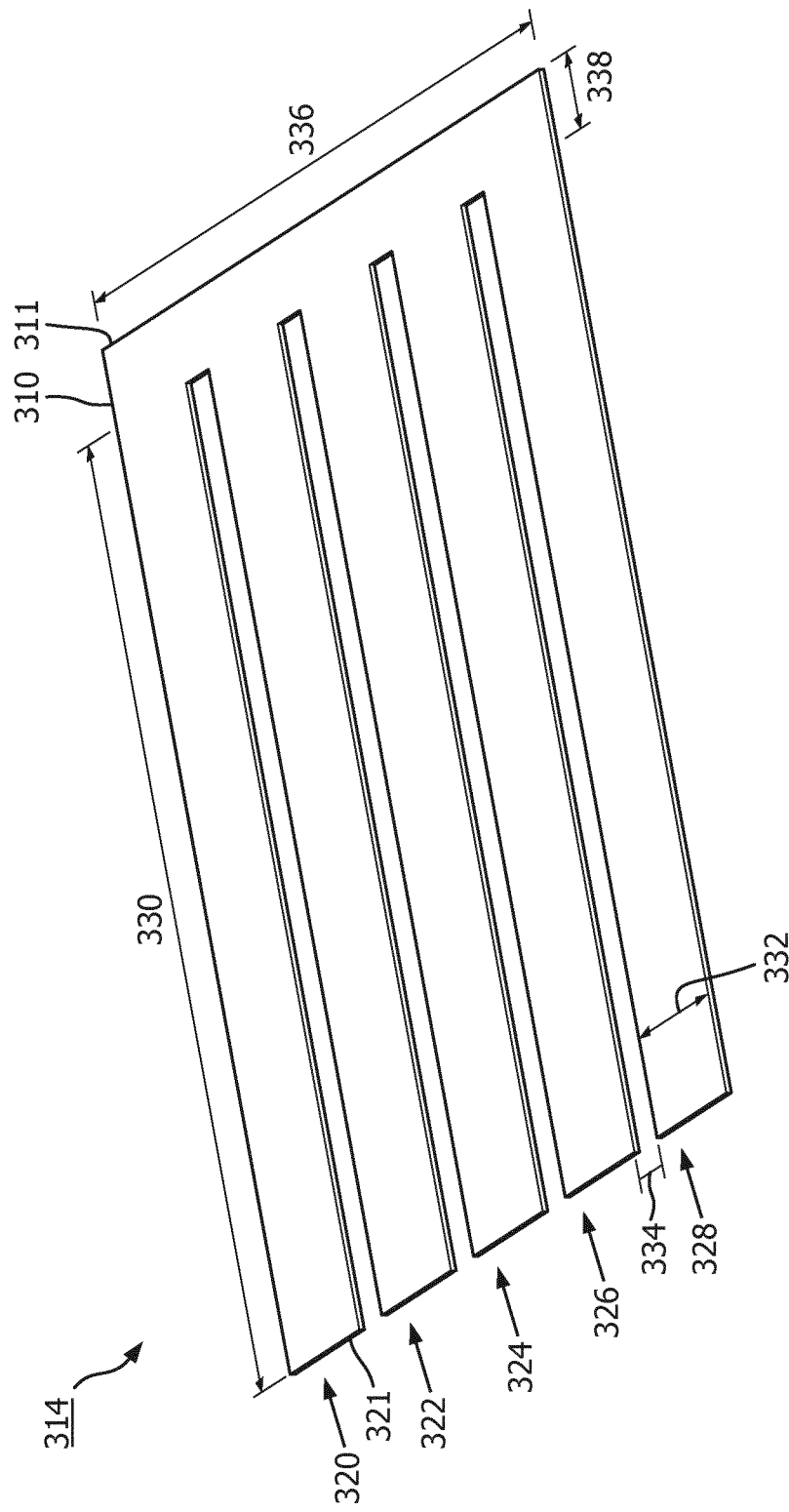
FIG. 5 is a diagrammatic perspective view of a flex circuit in a flat configuration, according to aspects of the present disclosure.
Figure 6:
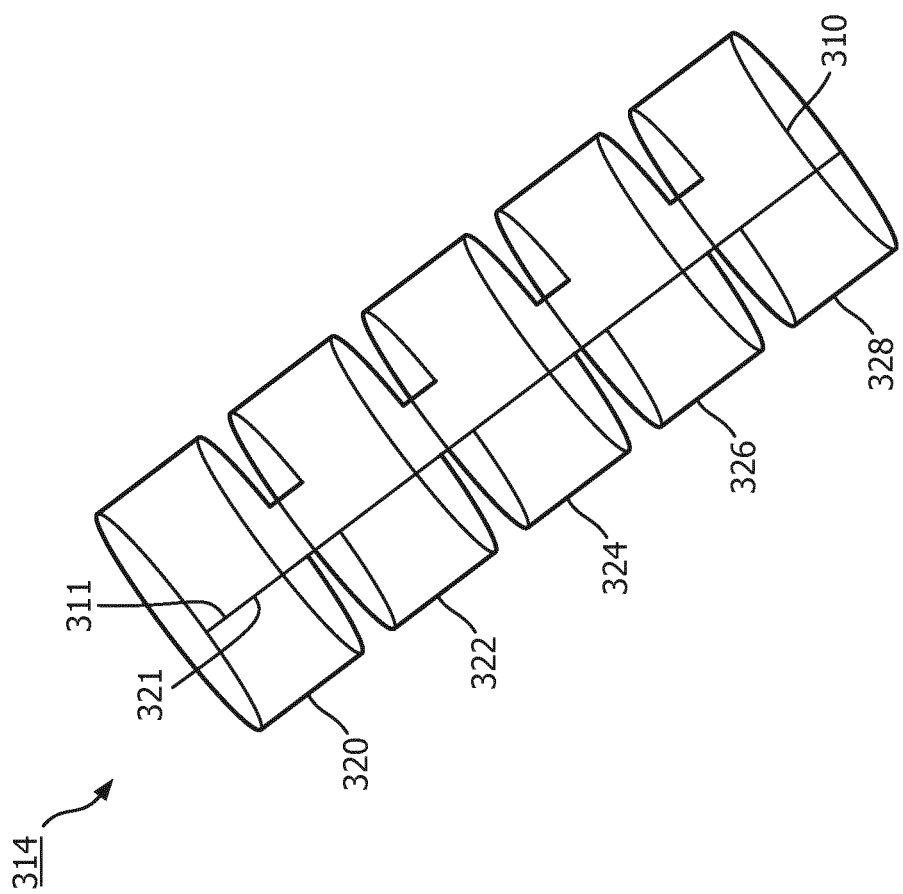
FIG. 6 is a diagrammatic perspective view of a flex circuit in a rolled configuration, according to aspects of the present disclosure.

FIGS. 5 and 6 illustrate an exemplary embodiment of a flex circuit 314 having a spine member 310 and rib members 320, 322, 324, 326, 328. The flex circuit 314 is disposed in a flat configuration in FIG. 5 and in a rolled configuration in FIG. 6. In some embodiments, the flex circuit 314 can be utilized within the imaging assembly 110 of IVUS device 102. The electrical cable 112 can be coupled to the flex circuit 314.

The flex circuit 314 includes a single spine member 310. As shown in FIG. 5, the spine member 310 is a generally rectangular-shaped region of the flex circuit 314. In other embodiments, spine member 310 may include alternative shapes, including linear, polygonal, ellipsoidal, and/or combinations thereof. The spine member 310 may be characterized by one or more dimensions 336, 338. A length 336 of the spine member 310 can be any suitable value, including between approximately 0.005" and 0.500", for example. A width 338 of the spine member 310 can be any suitable value, including between approximately 0.010" and 0.415", for example.

The flex circuit 314 includes multiple rib members, such as the rib members 320, 322, 324, 326, 328. The flex circuit 314 can include any suitable number of rib members, including two, three, four, five, six, seven, or more rib members. The embodiment of the flex circuit illustrated in FIGS. 5, 6, 7, and 9 includes five rib members. The illustrated embodiment of FIG. 10 includes three rib members. As shown in FIG. 5, each rib member 320, 322, 324, 326, 328 is a generally rectangular-shaped region of the flex circuit 314. In other embodiments, rib member 320, 322, 324, 326, 328 may include alternative shapes, including linear, polygonal, ellipsoidal, and/or combinations thereof. In that regard, each rib member 320, 322, 324, 326, 328 may have the same or different shape.

The rib members 320, 322, 324, 326, 328 may be characterized by one or more dimensions 330, 332. A length 332 of the rib member 328 can be any suitable value, including between approximately 0.025" and 0.250", for example. The rib members 320, 322, 324, 326 can have similar or different lengths. A width 330 of the rib member 320 can be any suitable value, including between approximately 0.081" and 0.415", for example. The rib members 322, 324, 326, 328 can have similar or different lengths.

The rib members 320, 322, 324, 326, 328 are spaced apart from one another by a distance 334. For example, when the IVUS device 102 is assembled, rib members 320, 322, 324, 326, 328 are longitudinally spaced from one another. The distance 334 can be any suitable value, including between approximately 0.005" and 0.1". As described in greater detail herein, the distance 334 can vary as the imaging assembly 110 bends/flexes while traversing vasculature within the patient body.

When the IVUS device 102 is assembled, the spine member 310 extends along the longitudinal axis LA (FIG. 1). For example, the spine member 310 can extend longitudinally in a direction parallel to the longitudinal axis LA. The rib members 320, 322, 324, 326, 328 extend from the spine member 310. In that regard, the rib members 320, 322, 324, 326, 328 extend from the spine member 310. For example, the rib members 320, 322, 324, 326, 328 extend perpendicularly from the spine member 310. The rib members 320, 322, 324, 326, 328 may extend in a direction transverse to the longitudinal axis LA. When the IVUS device 102 is assembled, the rib members 320, 322, 324, 326, 328 can at least partially circumscribe or extend around the longitudinal axis LA. That is, the rib members 320, 322, 324, 326, 328 from the spine member 310 can be disposed in a rolled configuration. The spine member 310 and the rib members 320, 322, 324, 326, 328 may be integrally formed and/or connected to define the flex circuit 314.

The spine member 310 includes an edge 311 on a lateral side of the flex circuit 314. Each of the rib members 320, 322, 324, 326, 328 includes an edge 321 on an opposite lateral side of the flex circuit 314. In the rolled configuration of the flex circuit 314 shown in FIG. 6, the edges 311, 321 are adjacent to and/or in contact with one another. Accordingly, the flex circuit 314 extends circumferentially around the longitudinal axis LA (FIG. 1).

Figure 7:
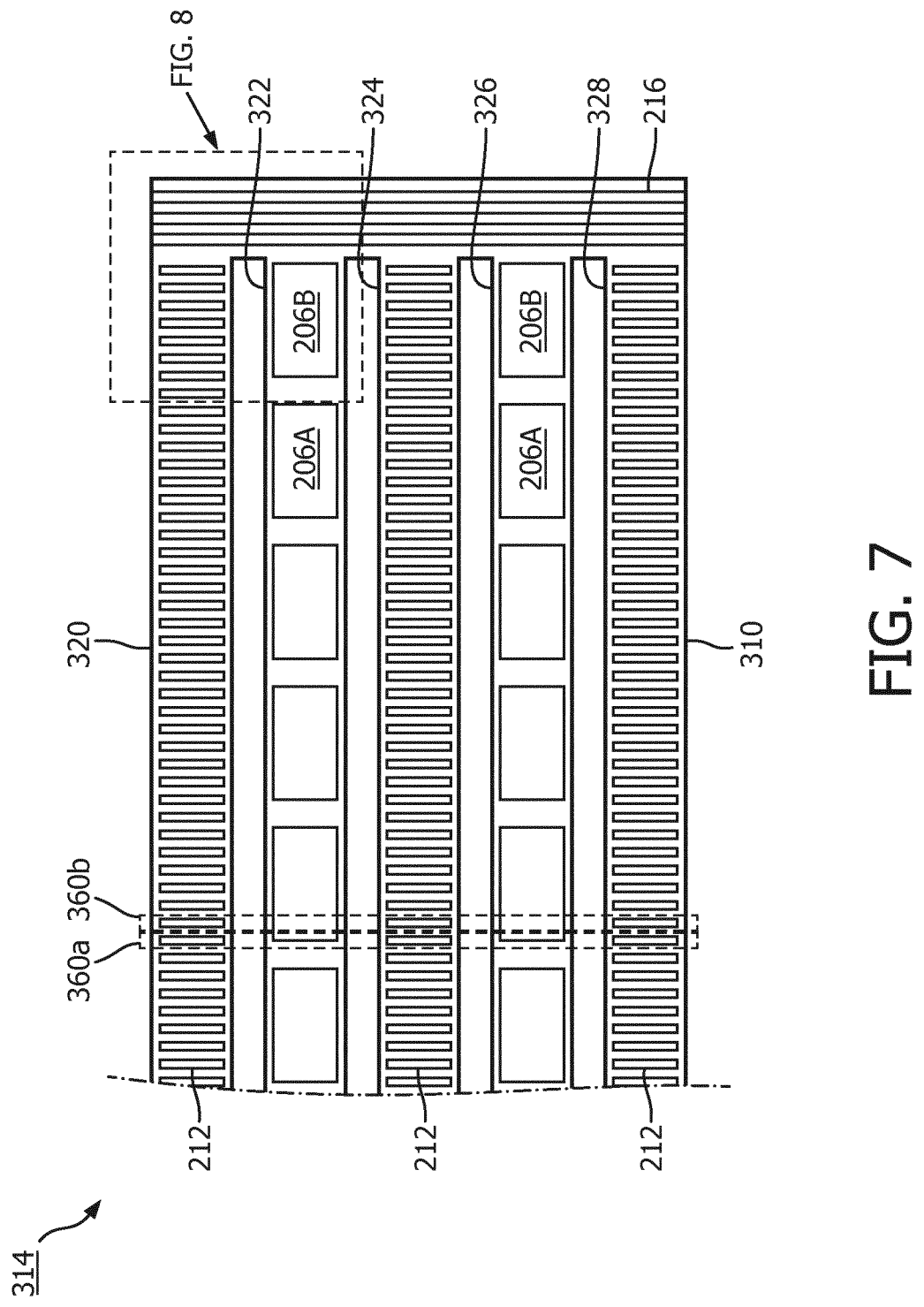
FIG. 7 is a diagrammatic top view of a scanner assembly in a flat configuration, according to aspects of the present disclosure.
Figure 8:
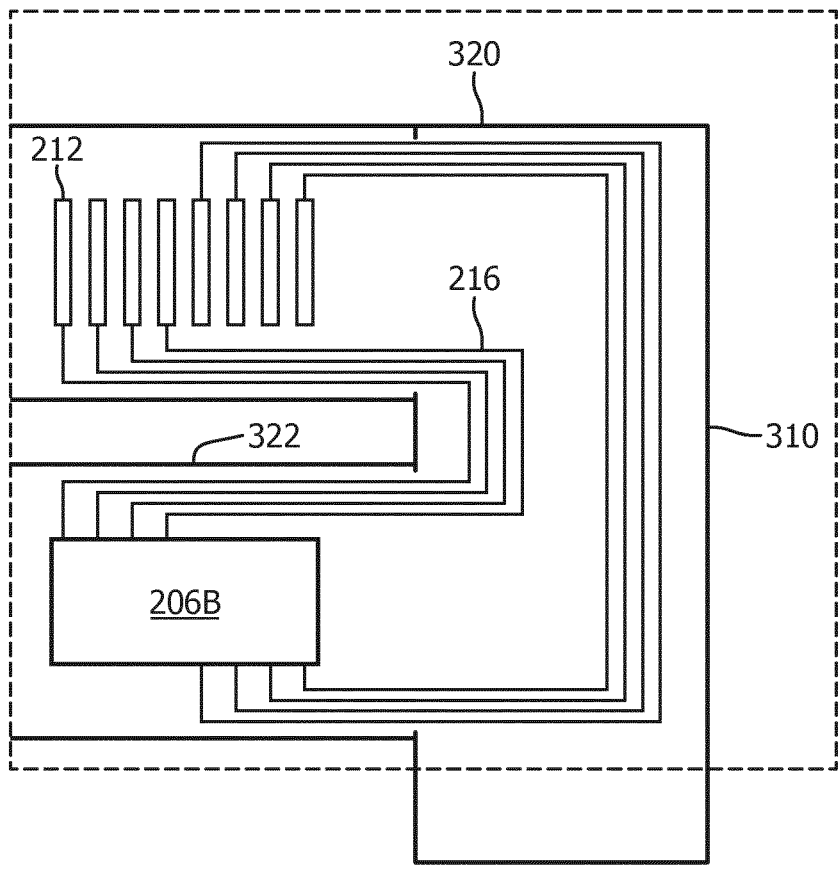
FIG. 8 is a diagrammatic top view of a portion of the scanner assembly of FIG. 7, according to aspects of the present disclosure.

FIGS. 7 and 8 illustrate additional features of the flex circuit 314. As shown, the rib members 320, 322, 324, 326, 328 can include transducer elements 212 and/or controllers 206A, 206B. The spine member 310, as well as the rib members 320, 322, 324, 326, 328, includes a plurality of conductive traces 216 that facilitate communication between the transducer elements 212 and/or the controllers 206A, 206B. The flex circuit 314 is in a flat configuration in FIGS. 7 and 8. FIG. 8 is a more detailed illustration of a region of the flex circuit 314 indicated in FIG. 7.

Any suitable number of rib members 320, 322, 324, 326, 328 can be populated by the transducers 212. In the embodiment of FIG. 7, three of the five rib members (rib members 320, 324, 328) include the transducers 212. In some embodiments, in the assembled IVUS device 102, the rib member 320 may be a distal-most rib member and the rib member 328 may be a proximal-most rib member. The rib member 324 may be a central rib member. Accordingly, in the illustrated embodiment, the flex circuit 314 includes transducers 212 on the distal-most rib member 320, the proximal-most rib member 328, and the central rib member 324. It understood that rib members 322 and 326 can be populated with transducers 212 in other embodiments.

Each of the rib members 320, 324, 328 can include a suitable number of transducers 212, only a portion of which are shown in FIG. 7 for clarity. For example, the rib members 320, 324, 328 can each include 32 or 64 transducer elements. In various embodiments, the rib members 320, 324, 328 can include the same or different number of transducers 212. Each of the transducer.

The transducers 212 can be any suitable type, including PZT transducers, CMUT transducers, and/or piezoelectric micromachined ultrasonic transducers (PMUT), for example. In some embodiments, the transducers 212 on each of the rib members 320, 324, 328 is the same type of transducer. In other embodiments, different types of transducers 212 can be positioned on each of the rib members 320, 324, 328. For example, the rib members 320, 324, 328 can include PZT transducers, CMUT transducers, and PMUT transducers, respectively. Such an arrangement would advantageously allow for the respective advantages associated with the different transducers types to be realized in a single device.

Any suitable number of rib members 320, 322, 324, 326, 328 can be populated by the controllers 206A, 206B. In the embodiment of FIG. 7, two of the five rib members (rib members 322, 326) include the controllers 206A, 206B. Accordingly, the rib members 320, 322, 324, 326, 328 alternatingly include the transducers 212 and the controllers 206A, 206B. In such embodiments, a rib member having transducers 212 is adjacent to a rib member having controllers 206A, 206B. The arrangement of transducers 212 and controllers 206A, 206B on the rib members 320, 322, 324, 326, 328 shown in FIG. 7 is exemplary. In that regard, the controllers 206A, 206B may be positioned on any of the rib members, including rib members 320, 324, 328. In the illustrated embodiments of FIGS. 7 and 8, the rib members 320, 322, 324, 326, 328 include only transducers 212 or only controllers 206A, 206B. In some embodiments, one or more of the rib members 320, 322, 324, 326, 328 include at least one transducer 212 and at least one controller 206A, 206B.

Each controller may be in communication with and/or configured to drive 4, 8, 16, and/or other suitable number of transducers. FIG. 8 illustrates the controller 206B in communication with eight transducers 212. In that regard, conductive traces 216 extend between the controller 206B and the eight transducers 212. The conductive traces 216 are electrically coupled to the controller 206B and the transducers 212 to facilitate electrical communication therebetween. The conductive traces 216 can be disposed on the spine member 310, as well as on the rib members 320, 322, 324, 326, 328. In some embodiments, the spine member 310 includes only conductive traces 216. In other embodiments, the spine member 310 can include one or more transducers 212, controllers 206A, 206B, and/or other electronic component(s). Each of the rib members 322, 326 can include a suitable number of controllers 206A, 206B, including 8, 9, 16, 17 and more in various embodiments.

While FIG. 8 shows the controller 206B in communication with transducers 212 on the same rib member, it is understood that the controller 206B can control transducers 212 on different rib members. Additionally, while FIG. 8 shows the controllers 206B in communication with transducers 212 on an adjacent rib member, it is understood the controller 206B can control transducers 212 on non-adjacent rib members. For example, the controller 206B on rib member 322 can control one or more transducers 212 on the rib member 328.

The computer 106 (FIG. 1) and/or the controllers 206A, 206B are operable to individually control each of the transducer elements 212 to emit ultrasound energy and/or receive ultrasound echoes associated with the emitted energy. In some instances, the respective array of transducer elements 212 on each of the ribs 320, 324, 328 can be operated as an individual transducer array 124 (FIG. 2). The computer 106 and/or the controllers 206A, 206B can transmit control signals to the step through the transducer elements 212 on the ribs 320, 324, 328 to obtain imaging data within the vessel. Because the ribs 320, 324, 328 are longitudinally spaced from one another, the ribs 320, 324, 328 can image regions within the vessel of the patient that are also spaced from one another. The computer 106 can generate multiple individual intraluminal images from the respective imaging data from the ribs 320, 324, 328. For example, individual intraluminal images of the spaced regions within the vessel can be generated. In some instances, the computer 106 combines imaging data obtained by the ribs 320, 324, 328 to generate one or more intraluminal images. For example, the ultrasound transmission area associated with the ribs 320, 324, 328 within the patient vessel may overlap. The computer 106 may utilize overlapping data to enhance one or more intraluminal images.

In some embodiments, the computer 106 and/or the controllers 206A, 206B are operable to simultaneously obtain imaging data via the ribs 320, 324, 328. In such embodiments, regions within the patient vessel that are spaced apart are simultaneously imaged by the ribs 320, 324, 328. In other embodiments, the computer 106 and/or the controllers 206A, 206B are operable to independently obtain imaging data from the ribs 320, 324, 328. For example, the ribs 320, 324, 328 may be controlled at different times to emit ultrasound energy and receive ultrasound echoes. For example, imaging data may be obtained first by the transducer elements 212 on rib 320, then by the transducer elements 212 on the rib 324, and finally by the transducer elements 212 on the rib 328, or any other suitable order.

In some instances, the computer 106 (FIG. 1) and/or the controllers 206A, 206B are operable to control groups of individual transducers 212, positioned on multiple rib members, to fire simultaneously. By selecting groups of individual transducers 212 on multiple rib members, the computer 106 (FIG. 1) and/or the controllers 206A, 206B can modify the emitted ultrasound beam shape. In that regard, the conal transmission shapes of multiple individual transducers 212 can be used to collectively image a region within a vessel that could not be imaged by an individual transducer alone. Exemplary groups 360$a$, 360$bs$ are identified in FIG. 7. In that regard, the transducers 212 of the group 360$a$, 360$b$ are aligned across the rib members 320, 324, 328. That is, the groups 360$a$, 360$b$ may be characterized as a column or row of transducers 212. The computer 106 (FIG. 1) and/or the controllers 206A, 206B can obtain imaging data by consecutively activating group 360$a$, then group 360$b$, and so on. Groups of non-aligned transducers 212 can also be simultaneously activated to obtain imaging data.

Figure 9:
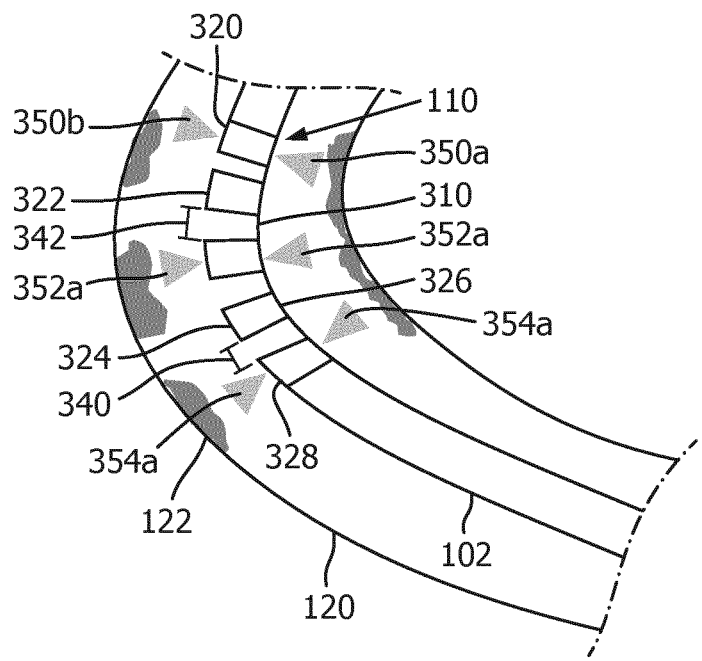
FIG. 9 is a diagrammatic illustration of an intraluminal imaging device in situ within a vessel of a patient, according to aspects of the present disclosure.

FIG. 9 illustrates the imaging device 102 in situ within the vessel 120. The imaging assembly 110 is shown to be flexed as the imaging device 102 traverses a bend in the vessel 120. Physiological obstructions 122, such as plaque, a lesion, a stenosis, and/or other blockage, are positioned within the vessel 120 and impede the flow of fluid, such as blood, within the vessel 120. The imaging assembly 110 can obtain imaging data while positioned within the vessel 120 and/or proximate to the obstructions 122. The transducers positioned on the rib member 320 are configured to image areas 350$a$, 350$b$ within the vessel 120. The transducers positioned on the rib member 324 are configured to image areas 352$a$, 352$b$ within the vessel 120. The transducers positioned on the rib member 328 are configured to image areas 354$a$, 354$b$ within the vessel 120. It is understood that the areas 350$a$, 350$b$, 352$a$, 352$b$, 354$a$, 354$b$ are exemplary only. In that regard, the rib members 320, 324, 328 are each operable to image a circumferential region within the vessel 120. As described above, the computer 106 (FIG. 1) and/or the controllers 206A, 206B are operable to control the rib members 320, 324, 328 and/or individual transducer element(s) of the rib members 320, 324, 328 to obtain imaging data simultaneously or independently, such as at different times.

The spine/rib structure of the flex circuit advantageously allows for the imaging even in tortuous areas of vasculature. When the imaging assembly contacts with a wall of the vessel 120 with conventional NUS imaging, the ability of the imaging elements to obtain a clear cross-sectional image of the vessel 120 is inhibited. According to the present disclosure, while the imaging assembly 110 may still contact the wall of the vessel 120 and prevent one or more of the rib members 320, 324, 328 from obtaining clear imaging data, at least one of the rib members 320, 324, 328 is likely to remain positioned within the vessel 120 to obtain imaging data that generates a diagnostically helpful intraluminal image. Additionally, the imaging data from the rib members 320, 324, 328 may be combined to generate one or more intraluminal images.

The increased flexibility and maneuverability of the imaging assembly 110 within the vessel 120 is shown in FIG. 9. In that regard, the separation between the rib members 320, 322, 324, 326, 328 can vary as the imaging assembly 110 moves through the bend in the vessel 120. For example, the central portion of the imaging assembly can be flexed to a greater degree than a distal portion in the illustrated embodiment. Accordingly, a distance 342 between the rib members 322, 324 can be greater than a distance 340 between the rib members 326, 328. In various embodiments, the distances 340, 342, associated with the rib member spacing while the imaging assembly 110 is being flexed, may be greater than or less than the distance 334 (FIG. 5), associated with rib member spacing when the imaging assembly 110 is not being flexed.

Figure 10:
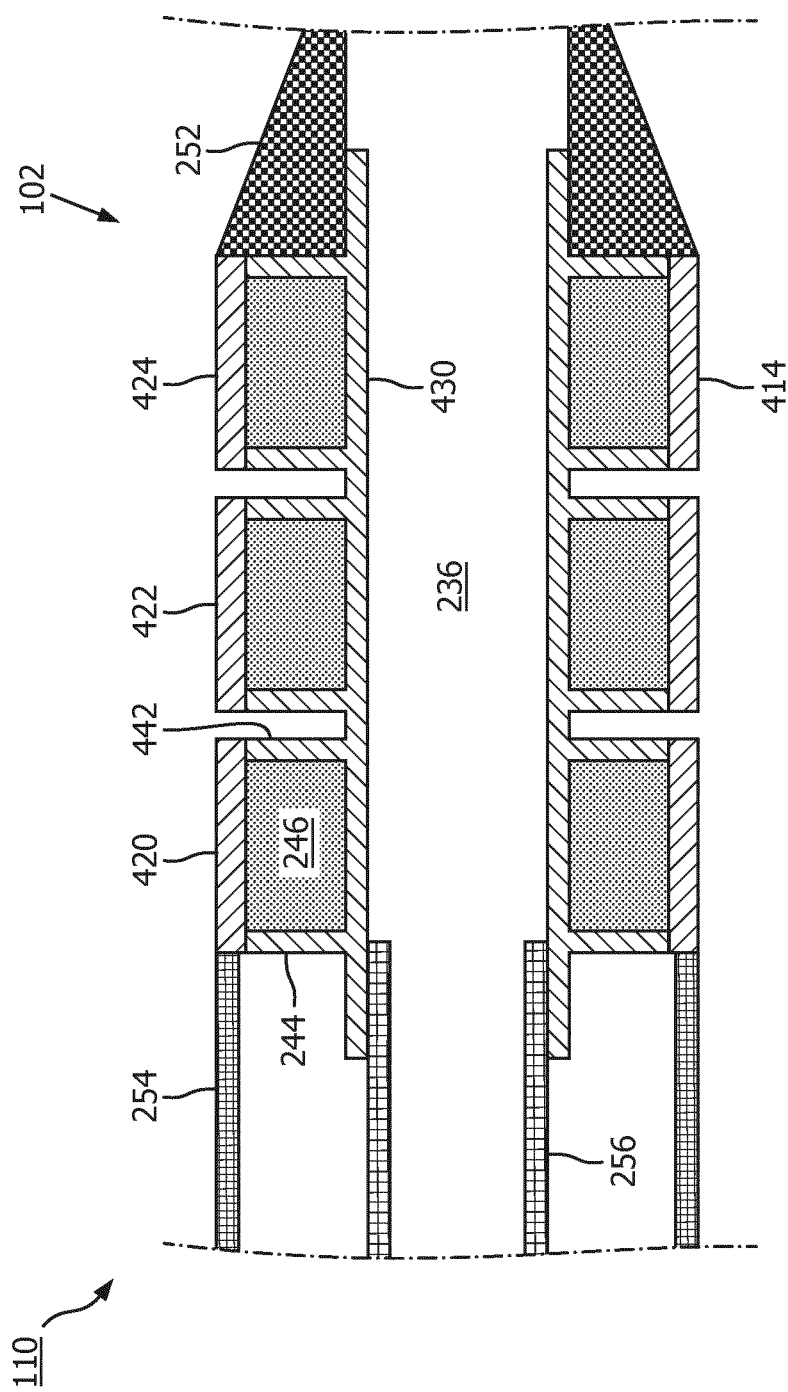
FIG. 10 is a diagrammatic side view of a scanner assembly in a rolled configuration, according to aspects of the present disclosure.

FIG. 10 is a cross-sectional view of the distal portion of the imaging device 102. The imaging assembly 110 includes a flex circuit 414 having a spine member and three rib members 420, 422, 424. FIG. 10 includes several features similar to those shown in FIG. 4. The flex circuit 414 is positioned in a rolled configuration around a support member 430. In the illustrated embodiment, the structure of the support member 430 matches the spine/rib structure of the flex circuit 414. In the regard, the support member 430 includes multiple stands 442, 444 defining areas on which the rib members 420, 422, 424 are positioned. Each rib member 420, 422, 424 is in contact with two stands 442, 444. The support member 430 can be manufactured according to any suitable process, including 3D printing and/or micro injection molding. The support member 430 may be manufactured using a flexible non-metallic material, such as a plastic or polymer. The acoustic backing material 246 is disposed within the space between the stands and the rib members 420, 422, 424. In some embodiments, structure of the support member 430 does not match spine/rib structure of the flex circuit 414. For example, the flex circuit 414 can be positioned around a cylindrically-shaped, flexible support member 430, as described in U.S. Provisional Application No. 61/985,220, "Pre-Doped Solid Substrate for Intravascular Devices," filed Apr. 28, 2014, the entirety of which is hereby incorporated by reference herein.

Figure 11:
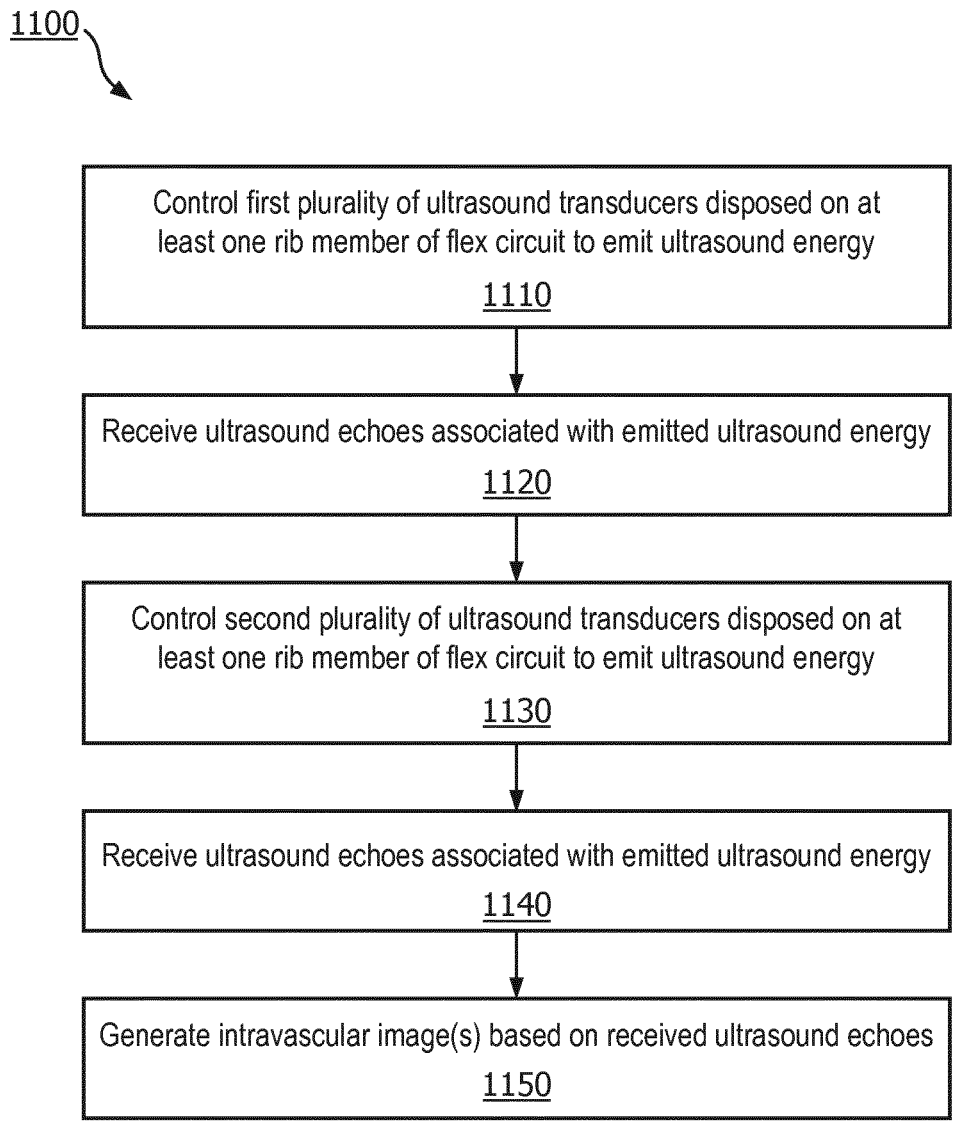
FIG. 11 is a flow diagram of a method of intraluminal imaging, according to aspects of the present disclosure.

FIG. 11 is a flow diagram of a method 1100 of intraluminal imaging. It is understood that the steps of method 1100 may be performed in a different order than shown in FIG. 11, additional steps can be provided before, during, and after the steps, and/or some of the steps described can be replaced or eliminated in other embodiments. The steps of the method 1100 can be carried out a computing device, such as the computer 106 (FIG. 1).

At step 1110, the method 1100 includes controlling a first plurality of ultrasound transducers disposed on at least one rib member of the flex circuit to emit ultrasound energy. The first plurality of ultrasound transducers can be disposed on a single rib member or on multiple rib members. At step 1120, the method 1100 includes receiving ultrasound echoes associated with the emitted ultrasound energy.

At step 1120, the method 11 includes controlling a second plurality of ultrasound transducers disposed on at least one rib member of the flex circuit to emit ultrasound energy. The second plurality of ultrasound transducers can be disposed on a single rib member or on multiple rib members. At step 1140, the method 1100 includes receiving ultrasound echoes associated with the emitted ultrasound energy.

In some instances, the first plurality of ultrasound transducers (step 1110) can be associated with a first rib member, and the second plurality of ultrasound transducers (step 1130) can be associated with a second rib member. In other instances, the first and second pluralities of ultrasound transducers are each associated with two or more rib members. For example, the first plurality of ultrasound transducers can be a column or row of aligned transducers across multiple rib members. The second plurality of ultrasound transducers can be another column or row of aligned transducers across multiple rib members. The first and second pluralities of ultrasound transducers can be different groupings of ultrasound transducers on one or more rib members.

In some embodiments, the step 1130 can include controlling the second plurality of ultrasound transducers independently of the first plurality of ultrasound transducers. In some embodiments, the step 1130 can include controlling the second plurality of ultrasound transducers simultaneously as the first plurality of ultrasound transducers.

At step 1150, the method 1100 includes generating one or more IVUS images based on the received ultrasound echoes. When the imaging assembly includes ultrasound transducers positioned on multiple rib members, multiple IVUS images can be generated. Each IVUS image can be representative of the region of the vessel in which the respective rib member is located. In some instances, the imaging data obtained by multiple rib members can be combined to generate the one or more IVUS images.

Figure 12:
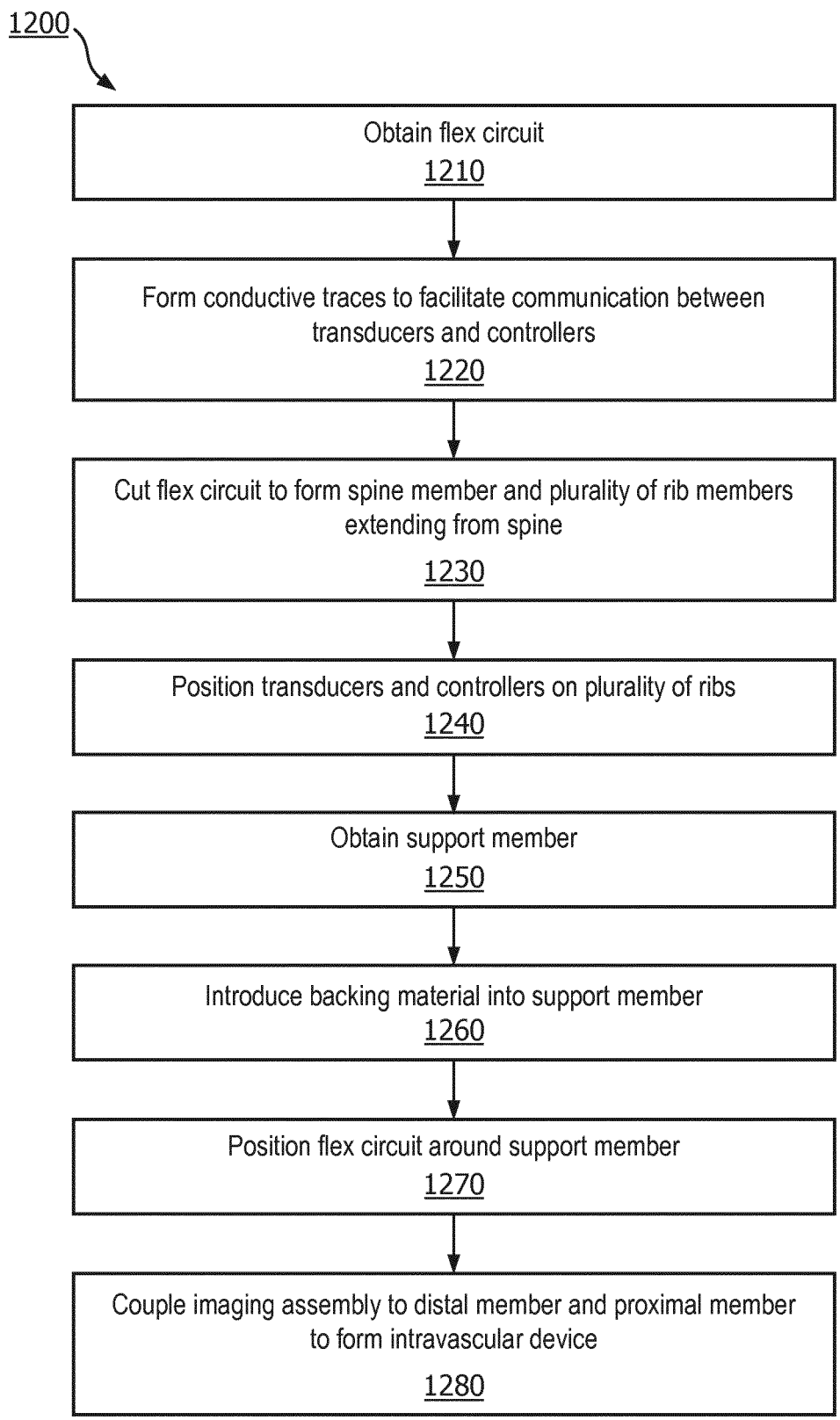
FIG. 12 is a flow diagram of a method of assembly an intraluminal imaging device, according to aspects of the present disclosure.

FIG. 12 is a flow diagram of a method 1200 of assembling an intraluminal imaging device, including an imaging assembly with a flex circuit having a spine member and rib members, as described herein. It is understood that the steps of method 1200 may be performed in a different order than shown in FIG. 12, additional steps can be provided before, during, and after the steps, and/or some of the steps described can be replaced or eliminated in other embodiments. The steps of the method 1200 can be carried out by a manufacturer of the intraluminal imaging device.

At step 1210, the method 1200 includes obtaining a flex circuit. The shape of the flex circuit at step 1210 maybe substantially rectangular. That is, at step 1210, the flex circuit does not have a spine member and/or rib members.

At step 1220, the method 1200 includes forming conductive traces on the flex circuit. The conductive traces will facilitate electrical communication between the ultrasound transducers and electronic controllers that will be disposed on the flex circuit (step 1240). The conductive traces can be formed on areas of the flex circuit that will become the spine member and rib members (step 1230). Any suitable process may be used for step 1220, including deposition.

At step 1230, the method 1200 includes cutting the flex circuit to form a spine member and multiple rib members extending from the spine member. Any suitable process may be utilized for step 1230, including laser cutting. Step 1230 may remove areas of the flex circuit between adjacent rib members such that the rib members are spaced from one another.

At step 1240, the method 1200 includes positioning ultrasound transducers and electronic controllers for the ultrasound transducers on the rib members. Any suitable process may be utilized for step 1240, including pick and place processes to locate and secure the transducers and controllers on the rib members. The transducers and controllers can be secured to the flex circuit using adhesive, solder, and/or other suitable component/process.

At step 1250, the method 1200 includes obtaining a support member. In some embodiments, obtaining the support member can include 3D printing or microinjection molding the support member. In that regard, the structure of the support member may match the spine/rib structure of the flex circuit. The support member can be made up of thin walls, with an open end of the support member face the inner diameter of the flex circuit. In other instances, the support member may be cylindrical and not include structure matching that of the spine and rib members of the flex circuit.

In embodiments in which acoustic backing material is required, at step 1260, the method 1200 includes introducing the backing material into the support member. For example, the backing material may be introduced into an open end of the support member that faces the inner diameter of the flex circuit. Step 1260 is omitted in embodiments in which the backing material is not required.

At step 1270, the method 1200 includes positioning the flex circuit around a support member to form an imaging assembly of the intraluminal device. The flex circuit may initially be in a flat configuration. Step 1270 can include transitioning at least a portion of the flex circuit into a rolled configuration around the support member. In embodiments in which the support members structures matches the structures of the spine member and rib members of the flex circuit, the step 1270 can also include aligning the flex circuit with the support member. The flex circuit is positioned around the support member such that the inner diameter of the flex circuit contacts the backing material. The method 1200 may include securing the flex circuit to the support member using one or more adhesives. The method 1200 may also include include curing the backing material, such as by using heat or light.

At step 1280, the method 1200 includes coupling the imaging assembly to one or more distal members and one or more proximal members to form the intraluminal device. In that regard, the distal member(s) and/or proximal member(s) can be coupled to the support member and/or the flex circuit. The one or more proximal members may be flexible elongate members (e.g., an inner member and/or an outer member) forming a length of the intraluminal device. The imaging assembly may be positioned at a distal portion of the intraluminal device. The distal member defines a distal-most end of the intraluminal imaging device. The method 1200 can include introducing adhesive to affix the flex circuit and the support member and/or other components of the intraluminal imaging device.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An intraluminal imaging device, comprising:
a flexible elongate member configured for insertion into a blood vessel of a patient, the flexible elongate member including a longitudinal axis, a proximal portion1 and a distal portion; and
an imaging assembly comprising a flex circuit disposed in a rolled configuration at the distal portion of the flexible elongate member, the flex circuit comprising:
a spine member extending along the longitudinal axis;
a plurality of rib members extending from the spine member and transverse to the longitudinal axis, wherein the plurality of rib members are spaced apart from one another along the longitudinal axis such that the imaging assembly is configured to flex between the plurality of rib members; and
a plurality of conductive traces different than the spine member and the plurality of rib members.

2. The device of claim 1, wherein:
at least one of the plurality of rib members comprises a plurality of ultrasound transducers,
at least one of the plurality of rib members comprises a plurality of controllers,
the spine member comprises the plurality of conductive traces,
the plurality of conductive traces facilitate communication between the plurality of the ultrasound transducers and the plurality of controllers.

3. The device of claim 2, wherein a proximal-most rib member and a distal-most rib member of the plurality of rib members comprises a plurality of ultrasound transducers.

4. The device of claim 2, wherein a central rib member of the plurality of rib members comprises a plurality of ultrasound transducers.

5. The device of claim 2, wherein the plurality of rib members comprises five rib members.

6. The device of claim 2, wherein different ones of the plurality of rib members of the flex circuit comprise different types of ultrasound transducers.

7. The device of claim 1, wherein the plurality of rib members extend around the longitudinal axis of the imaging assembly.

8. The device of claim 1, wherein the spine member comprises a polymer material that is continuous along the longitudinal axis.

9. The device of claim 8, wherein the plurality of rib members are spaced apart from one another by gaps in the polymer material.

10. The device of claim 9, wherein the plurality of conductive traces are spaced apart from one another by portions of the polymer material.

* * * * *